United States Patent [19]

Dickens et al.

[11] Patent Number: 4,628,104
[45] Date of Patent: Dec. 9, 1986

[54] IMIDAZOLE KETONE DERIVATIVES

[75] Inventors: Jonathan P. Dickens; William R. McKay, both of High Wycombe, United Kingdom

[73] Assignee: G. D. Searle & Co., Skokie, Ill.

[21] Appl. No.: 720,917

[22] Filed: Apr. 8, 1985

[51] Int. Cl.$^4$ .................. C07D 233/54; C07D 249/08; C07D 233/66; C07D 401/00
[52] U.S. Cl. .................................. 548/341; 546/276; 548/262; 548/337
[58] Field of Search ................ 546/276; 548/262, 341, 548/337

[56] References Cited

U.S. PATENT DOCUMENTS

| | | | |
|---|---|---|---|
| 4,107,314 | 8/1978 | Cox et al. | 548/262 |
| 4,144,346 | 3/1979 | Heeres et al. | 548/262 |
| 4,223,036 | 9/1980 | Heeres et al. | 548/262 |
| 4,377,697 | 3/1983 | Fellner et al. | 548/262 |

FOREIGN PATENT DOCUMENTS

| | | | |
|---|---|---|---|
| 117578 | 6/1984 | European Pat. Off. | 548/262 |
| 2067993 | 8/1981 | United Kingdom | 548/262 |

OTHER PUBLICATIONS

Drugs, 1975, 9, 406, Sawyer, et al.

Primary Examiner—Henry R. Jiles
Assistant Examiner—Robert C. Whittenbaugh
Attorney, Agent, or Firm—Steven Odre

[57] ABSTRACT

This disclosure relates to a class of novel compounds of the formula:

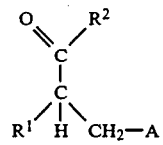

wherein
$R^1$ is $C_1$-$C_4$ alkyl, phenyl or $C_1$-$C_4$ alkylphenyl;
$R^2$ is $C_1$-$C_7$ alkyl, benzyl, pyridyl, phenyl, halophenyl or dihalophenyl; and
A is imidazol-1-yl, 1,2,4-triazol-1-yl or substituted imidazol-1-yl wherein the substituent is one or more groups selected from class consisting of $C_1$-$C_4$ alkylthio and carboxy($C_2$-$C_4$ alkenyl);

and pharmaceutically acceptable acid addition salts thereof. This invention further relates to pharmaceutical compositions containing the compounds and to the use of such compounds and compositions as anti-anaerobic agents.

2 Claims, No Drawings

IMIDAZOLE KETONE DERIVATIVES

BACKGROUND OF THE INVENTION

The present invention related to a class of novel imidazole ketone derivatives. The invention further relates to pharmaceutical compositions containing such compounds and to the use of such compounds and compositions as anti-anaerobic agents.

Various azole derivatives are useful as anti-fungal agents. U.S. Pat. No. 4,107,314 describes a class of heterocyclic thioalkyl substituted imidazole derivatives useful as anti-anaerobic agents. U.S. Pat. Nos. 4,144,346 and 4,223,036 describe a class of 1-(1,3-dioxolan-2-ylmethyl)-1H-imidazoles and 1-(1,3-dioxolan-2-ylmethyl)-1H-1,2,4-triazoles respectively, which are useful as anti-fungal and anti-bacterial agents. Miconazole, described by P. R. Sawyer, R. N. Brogden, R. M. Pinder, T. M. Speight and G. S. Avery, *Drugs*, 1975, 9, 406, is a topical and intravenous anti-fungal agent. European Patent Application No. 117578 describes a class of azole-substituted alcohol derivatives. UK Pat. No. 2067993 describes a class of imidazole hydrazone derivatives useful as anti-anaerobic agents. U.S. Pat. No. 4,377,697 describes a class of imidazole hydrazone and hydrazine derivatives useful as anti-anaerobic and anti-fungal agents.

SUMMARY OF THE INVENTION

This disclosure relates to a class of novel compounds of the formula:

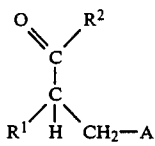

(I)

wherein
$R^1$ is $C_1$–$C_4$ alkyl, phenyl or $C_1$–$C_4$ alkylphenyl;
$R^2$ is $C_1$–$C_7$ alkyl, benzyl, pyridyl, phenyl, halophenyl or dihalophenyl; and
A is imidazol-1-yl, 1,2,4-triazol-1-yl or substituted imidazol-1-yl wherein the substituent is one or more groups selected from class consisting of $C_1$–$C_4$ alkylthio and carboxy($C_2$–$C_4$ alkenyl); and pharmaceutically acceptable acid addition salts thereof.

This invention further relates to pharmaceutical compositions containing the compounds of formula (I) and to the use of such compounds and compositions as anti-anaerobic agents, such as in the treatment of peridontal disease.

In addition certain intermediates in the process for producing such compounds of formula (I) are also useful as anti-anaerobic agents.

DETAILED DESCRIPTION OF THE INVENTION

The "$C_1$–$C_4$ alkyl" and "$C_1$–$C_7$ alkyl" groups specified herein include straight chain or branched chain hydrocarbon radicals having from one to four and from one to seven carbon atoms respectively. Illustrative of such $C_1$–$C_4$ alkyl radicals include methyl, ethyl, propyl, isopropyl, butyl, isobutyl, sec-butyl and tert-butyl. Illustrative of such $C_1$–$C_7$ alkyl radicals include methyl, ethyl, propyl, isopropyl, butyl, isobutyl, sec-butyl, tert-butyl, pentyl, neopentyl, hexyl, isohexyl, heptyl, and the like.

As used herein the terms "halogen" or "halo" refer to fluoro, chloro, bromo and iodo.

The term "substituted imidazol-1-ly" refers to an imidazol-1-yl radical having a substituent selected from the group consisting of $C_1$–$C_4$ alkylthio and carboxy ($C_2$–$C_4$ alkenyl). Representative of such substituted imidazol-1-yl radicals include for example methylthioimidazol-1-yl, ethylthioimidazol-1-yl, carboxyethenylimidazol-1-yl and the like. The compounds of formula (I) may be prepared in accordance with one of the following synthetic routes:

As used herein the terms "halophenyl" and "dihalophenyl" refer to a phenyl radical substituted with one or two halogen substitutents respectively. Representative of halophenyl moieties includes fluorophenyl, chlorophenyl, iodophenyl and bromophenyl. It is preferred that the halogen substitutent be in the 2- or 4- position of the phenyl radical. Representative of dihalophenyl moieties include difluorophenyl, dichlorophenyl, dibromophenyl, chlorobromophenyl, fluorochlorophenyl, iodobromophenyl and the like. It is preferred that the halogen substitutents be in the 2,4- or 3,5-positions of the phenyl radical. The compounds of the present invention may be prepared in accordance with the following procedure:

An alcohol of the formula

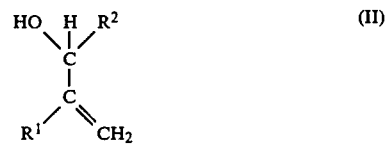

(II)

wherein $R^1$ and $R^2$ are above defined; is reacted with barium manganate or alternatively a mixture of oxalyl chloride and dimethylsulfoxide at a temperature of about −70° C., to yield a substituted ketone of the formula:

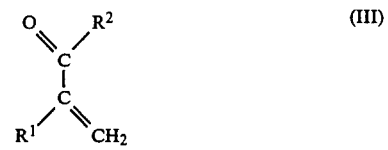

(III)

The substituted ketone of formula (III) is reacted with imidazole, triazole or a substituted imidazole to yield a compound of formula (I). It should be noted that certain substituted ketones of formula (III) are novel and may be useful as anti-anaerobic agents.

The alcohols of formula (II) utilized as starting materials may be prepared by reacting a 1-halo-1-substituted ethene of the formula

(IV)

wherein $R^1$ is above defined and X is halogen with magnesium under reflux to yield a magnesium halide of the formula

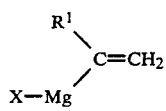 (V)

The magnesium halide of formula (V) is reacted with a substituted aldehyde of the formula

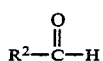 (VI)

to yield the alcohol of formula (II).

Alternatively, a substituted ethanone of the formula

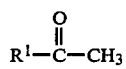 (VII)

wherein $R^1$ is above defined is reacted with a substituted phenylsulfonylhydrazine to yield a substituted hydrazone derivative of the formula

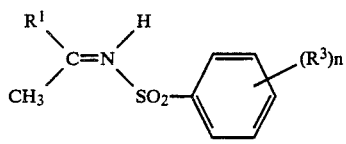 (VIII)

wherein $R^3$ is $C_1$–$C_4$ alkyl and n is an integer of from 0 to 3. An alkyllithium is added to the reaction mixture at a temperature less than −60° C., followed by the addition of a substituted aldehyde of the formula

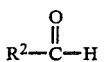 (IX)

to yield the alcohol of formula (II).

The temperatures at which the above reactions are conducted are not critical. It is preferred to conduct the above reactions at a temperatures sufficient to allow the reactions to proceed towards completion. Such temperatures vary from reaction to reaction and are readily ascertained by one of ordinary skill in the art.

The appropriate solvents employed in the above reactions are solvents wherein the reactants are soluble but do not react with the reactants. The preferred solvents vary from reaction to reaction and are readily ascertained by one of ordinary skill in the art.

The compounds of formula (I) form acid addition salts with inorganic acid such as hydrohalogenic acid (e.g., hydrochloric acid, hydrobromic acid), sulfuric acid, phosphoric acid, succinic acid, glycolic acid, lactic acid, gluconic acid, tartaric acid, citric acid, maleic acid, malic acid, fumaric acid, methanesulfonic acid, p-toluene-sulfonic acid, oxalic acid, ascorbic acid, benzoic acid or the like. The pharmaceutically acceptable acid addition salts are preferred.

The pharmaceutically acceptable addition salts of the compounds of the present invention may be prepared by conventional procedures, e.g., by reacting the free base in a suitable solvent, e.g., diethylether or ethanol, with a solution containing one equivalent of the desired acid in a suitable solvent, e.g., diethylether or ethanol. The salt generally precipitates from solution or is recovered by evaporation of the solvent.

The preferred embodiment of the present invention includes compounds of formula (I) wherein $R^1$ is $C_1$–$C_4$ alkyl, phenyl or $C_1$–$C_4$ alkylphenyl, $R^2$ is halophenyl or dihalophenyl, and A is imidazol-1-yl or substituted imidazol-1-yl. A more preferred embodiment of the present invention includes compounds of formula (I) wherein $R^1$ is phenyl, $R^2$ is dihalophenyl, and A is imidazol-1-yl or methylthioimidazol-1-yl. A most preferred embodiment of the present invention includes compounds of formula (I) wherein $R^1$ is phenyl, $R^2$ is dichlorophenyl and A is imidazol-1-yl or methylthioimidazol-1-yl.

The compounds of the present invention may be administered topically, preferably in the form of a pharmaceutical composition adapted to such a route, and in a dose effective for the treatment intended.

Accordingly, the invention provides a class of novel pharmaceutical compositions comprising one or more compounds of the present invention in association with one or more non-toxic, pharmaceutically acceptable carriers and/or diluents and/or adjuvants and if desired other active ingredients.

Representative carriers, diluents and adjuvants include for example water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

As indicated, the dose administered and the treatment regiment will be dependent, for example, on the disease, the severity thereof, on the patient being treated and his response to treatment and therefore may be widely varied.

The following Examples are intended to further illustrate the present invention and not to limit the invention in spirit or scope. In the Examples, all parts are parts by weight unless otherwise expressly set forth.

EXAMPLE 1

1-(2,4-Dichlorophenyl)-2-phenylpropen-1-one

A mixture containing magnesium metal (0.73 g) with 1-bromo-1-phenylethene was reacted in refluxing tetrahydrofuran (75 ml). A solution of 2,4-dichlorobenzaldehyde (4.7 g) in tetrahydrofuran (25 ml) was added to the reaction mixture and the resulting mixture was maintained at reflux for 4 hours. The reaction mixture was cooled, poured into dilute hydrochloric acid, and extracted with ethyl acetate. The organic phase was washed with water, dried over anhydrous magnesium sulfate and concentrated under reduced pressure to yield a gum (7 g), which was chromatographed on silica gel eluting with ethyl acetate: hexane (1:1) to yield α-(1-phenyl)ethenyl-2,4-dichlorobenzenemethanol (5 g).

To a solution, of the α-(1-phenyl)ethenyl-2,4-dichlorobenzene-methanol (4 g) in toluene (100 ml) was added barium manganate (5 g) and the resulting mixture heated to reflux under an atmosphere of nitrogen. After 12 hours the reaction mixture was cooled, filtered and concentrated under reduced pressure to yield 1-(2,4-dichlorophenyl)-2-phenylpropen-1-one. δ (CDCl₃), 5.75 (1H,S), 6.3 (1H,s) and 7.25–7.60 (8H,m) as a gum (4.3 g) having the formula:

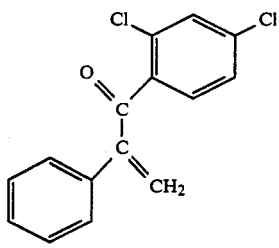

EXAMPLE 2

1-(2,4-Dichlorophenyl)-3-(imidazol-1-yl)-2-phenylpropan-1-one

A solution of 1-(2,4-dichlorophenyl)-2-phenylpropen-1-one (4 g), imidazole (1.36 g) and tetramethylguanidine (0.5 ml) in tetrahydrofuran (100 ml) was heated at reflux for 12 hours. The reaction mixture was cooled and concentrated under reduced pressure to yield a gum. The gum was dissolved in ethyl acetate, washed with distilled water, and acidified with 4N hydrochloric acid. The resulting aqueous phase was basified with sodium hydrogen carbonate and extracted with ethyl acetate. The organic phase was separated, washed with distilled water, dried over anhydrous magnesium sulfate and concentrated under reduced pressure to yield an oil which was chromatographed on silica gel in methanol/dichloromethane (1:9) to yield 1-(2,4-dichlorophenyl)-3-(imidazol-1-yl)-2-phenylpropan-1-one (600 mg), which was treated with ethereal hydrogen chloride to yield the hydrochloride salt of 1-(2,4-dichlorophenyl)-3-(imidazol-1-yl)-2-phenylpropan-1-one, m.p. 110° C., (Found: C, 55.38; H, 4.37; N, 7.40; $C_{18}H_{15}Cl_3N_2O.\frac{1}{2}H_2O$ requires C, 55.34; H, 4.13; N, 7.17) having the formula:

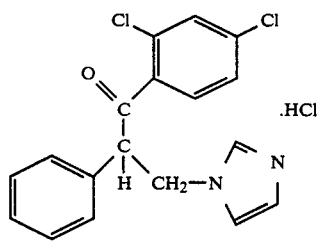

EXAMPLE 3

α-[1-(4-Methylphenyl)ethenyl]-2,4-dichlorobenzenemethanol 1-(4-Methylphenyl)ethanone (2.28 g) and concentrated hydrochloric acid (1 ml) were added to a stirred solution of 2,4,6-triisopropyl benzenesulphonylhydrazine (5 g) in methanol (20 ml). The resulting mixture was stirred until a dense white precipitate formed. The precipitate was removed by filtration and washed with cold methanol to yield 1-(4-methylphenyl)ethanone 2,4,6-triisopropylbenzenesulphonylhydrazone (6 g) as a fine white crystalline solid.

To a solution of 1-(4-methylphenyl)ethanone-2,4,6-triisopropylbenzenesulfonylhydrazone (6.54 g) in tetrahydrofuran (80 ml) at −70° C. was dropwise added a solution of methyl lithium (25 ml, 1.3M in ether) while stirring and maintaining the temperature of the mixture below −60° C. After 10 minutes the reaction mixture was allowed to warm to room temperature. When evolution of nitrogen from the reaction mixture ceased, a solution of 2,4-dichlorobenzaldehyde (3.48 g) in tetrahydrofuran (10 ml) was rapidly added. After stirring for 1 hour at room temperature the reaction was quenched with a saturated aqueous ammonium chloride solution. The reaction mixture was concentrated under reduced pressure. The resulting residue was dissolved in ethyl acetate, washed with saturated aqueous sodium hydrogen carbonate, washed with water, dried over anhydrous magnesium sulphate and concentrated under reduced pressure to yield an oil. The oil was chromatographed on silica gel eluting with ethyl acetate-hexane (3:97) to yield α-[1-(4-methylphenyl)ethenyl]-2,4-dichlorobenzenemethanol δ (CDCl₃): 1.86 (1H,d, J=5 Hz), 2.64–2.78 (1H, dd, J=13.5 Hz, J=10 Hz), 2.92–3.04 (1H,dd, J=15 Hz, J=5 Hz), 4.8 (1H,m), 5.38 (2H,d, J=6 Hz) and 7.16–7.5 (10H,m) as a yellow oil (2.1 g) having the formula:

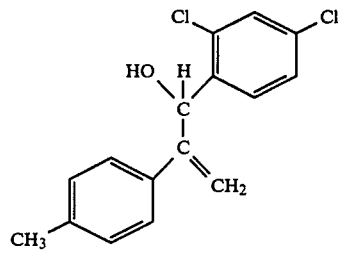

EXAMPLES 4–8

The procedure of Example 3 was conducted employing the appropriate starting materials to yield the following compounds:

EXAMPLE 4

2-(4-Methylphenyl)dec-1-en-3-ol δ(CDCl₃) 0.8–1.7 (15H,m), 2.38 (3H,s), 4.62 (1H,m), 5.30 (2H,d, J=10 Hz), 7.18 (2H,d, J=12 Hz) and 7.34 (2H,d, J=12 Hz) having the formula:

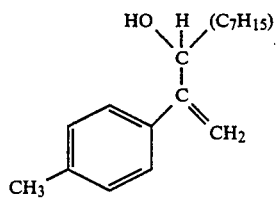

EXAMPLE 5

α-(1-Phenylethenyl)-3,5-dichlorobenzenemethanol δ (CDCl₃): 2.21 (1H,d, J=5 Hz), 5.44 (1H,s), 5.54 (1H,s), 5.65 (1H,d, J=5 Hz) and 7.22–7.34 (8H,m) having the formula:

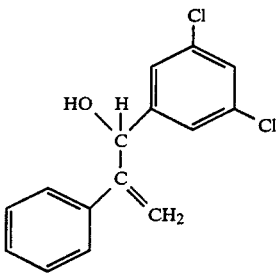

EXAMPLE 6

α-(1-Phenylethenyl)-3-pyridinemethanol δ (CDCl$_3$): 5.52 (2H,d, J=5 Hz), 5.76 (1H,s), 7.18–7.36 (6H,m), 7.72 (1H,m), 8.44 (1H,d, J=4.5 Hz) and 8.58 (1H,s) having the formula:

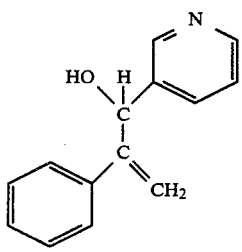

EXAMPLE 7

α-(1-Phenylethenyl)-2-pyridinemethanol δ (CDCl$_3$): 5.45 (2H,d, J=7.5 Hz), 5.66 (1H,s), 7.10–7.36 (6H,m), 7.44–7.66 (1H,m), 7.84–7.96 (1H,m) and 8.45–8.55 (1H,m) having the formula:

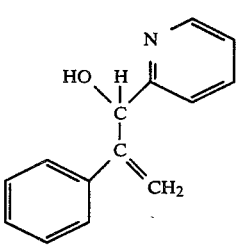

EXAMPLE 8

α-[1-(1,1-Dimethylethyl)ethenyl]-2,4-dichlorobenzenemethanol δ (CDCl$_3$): 1.12 (9H,s), 5.1 (1H,s), 5.26 (1H,s), 5.74 (1H,s) and 7.21–7.58 (3H,m) having the formula:

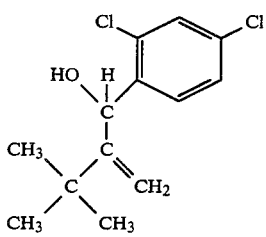

EXAMPLE 9

1-(2,4-Dichlorophenyl)-2-(4-methylphenyl)propen-1-one

To oxalyl chloride (1.01 g) in dichloromethane (10 ml) at −70° C. was added dimethylsulphoxide (1.23 g) in dichloromethane (6 ml). To the resulting mixture was dropwise added a solution of α-(1-phenylethenyl)-2,4-dichlorobenzenemethanol (2.07 g) in dichloromethane (6 ml). Triethylamine (2.17 g) was added to the reaction mixture and the resulting mixture was stirred for an additional 20 minutes and then allowed to warm to room temperature. The reaction mixture was washed with water and the organic phase separated and concentrated under reduced pressure. The resulting residue was redissolved in ethyl acetate, washed with water, dried over anhydrous magnesium sulphate. The solvent removed under reduced pressure to yield 1-(2,4-dichlorophenyl)-2-(4-methylphenyl)propen-1-one (δ (CDCl$_3$), 5.92 (1H,s) 6.16 (1H,s) and 7.1–7.3 (10H,m) p.p.m.) as an oil having the formula:

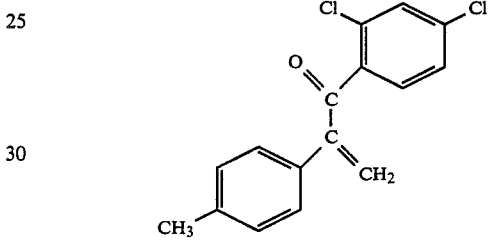

EXAMPLES 10–14

EXAMPLE 10

2-(4-Methylphenyl)dec-1-en-3-one δ (CDCl$_3$) 0.8–1.7 (15H,m), 2.38 (3H,s), 5.85 (1H,s), 6.05 (1H,s) and 7.16 (4H,m) having the formula:

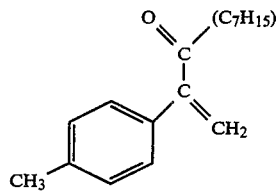

EXAMPLE 11

1-(3,5-Dichlorophenyl)-2-phenylpropen-1-one δ (CDCl$_3$) 5.66 (1H,s), 6.16 (1H,s), 7.32–7.44 (5H,m), 7.53 (1H,s) and 7.75 (2H,d, J=1 Hz) having the formula:

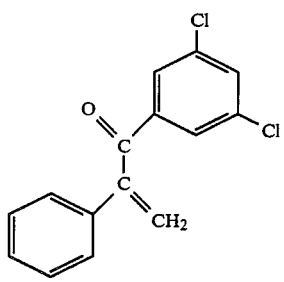

EXAMPLE 12

2-Phenyl-1-(3-pyridyl)propen-1-one δ (CDCl₃) 5.77 (1H,s), 6.18 (1H,s), 7.24–7.48 (6H,m), 8.14–8.26 (1H,m), 8.73–8.82 (1H,dd, J=5.5 Hz, J=1 Hz), and 9.06 (1H,d, J=1 Hz) having the formula:

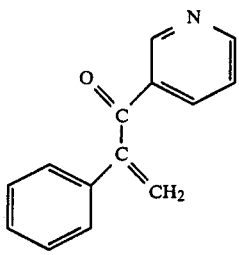

EXAMPLE 13

2-Phenyl-1-(2-pyridyl)propen-1-one δ (CDCl₃) 5.97 (1H,s), 6.21 (1H,s), 7.24–7.5 (6H,m), 7.82–7.92 (1H,m), 7.95–8.05 (1H,m) and 8.62–8.74 (1H,m) having the formula:

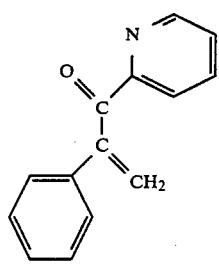

EXAMPLE 14

1-(2,4-Dichlorophenyl)-3,3-dimethyl-2-methylenebutan-1-one δ (CDCl₃) 1.31 (9.H,s), 5.52 (1H,s), 6.01 (1H,s) and 7.2–7.44 (3H,m) having the formula:

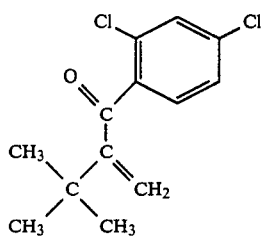

EXAMPLE 15

1-(2,4-Dichlorophenyl)-3-(imidazol-1-yl)-2-(4-methylphenyl) propan-1-one

A mixture of 1-(2,4-dichlorophenyl)-2-(4-methylphenyl)propen-1-one (660 mg) and imidazole (770 mg) in ethanol (10 ml) were stirred at room temperature for 16 hours. The reaction mixture was concentrated under reduced pressure, dissolved in ethyl acetate, washed with water, dried over anhydrous magnesium sulphate and concentrated under reduced pressure to yield a gum. The gum was chromatographed on silica gel in methanol: dichloromethane (1:24) to yield 1-(2,4-dichlorophenyl)-3-(imidazol-1-yl)-2-(4-methylphenyl)-propan-1-one (450 mg) (Found: C, 78.25; H, 5.88; N, 9.53; C₁₉H₁₈N₂O requires C, 78.62; H, 6.21; N, 9.66) which was treated with ethereal hydrogen chloride to yield the hydrochloride salt of 1-(2,4-dichlorophenyl)-3-(imidazol-1-yl)-2-(4-methylphenyl)propan-1-one m.p. 92°–96° C. (Found: C, 54.79; H, 4.33; N, 6.59; C₁₉H₁₇Cl₃N₂O.H₂O requires C, 55.16; H, 4.38; N, 6.77) having the formula:

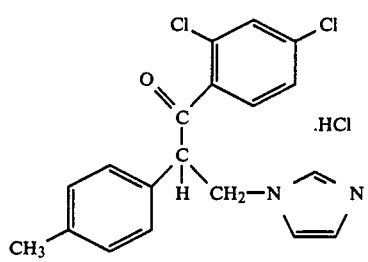

EXAMPLES 16–19

The procedure of Example 15 was conducted employing the appropriate starting material to yield the following compounds:

EXAMPLE 16

1-(2,4-Dichlorophenyl)-2-(4-methylphenyl)-3-(1,2,4-triazol-1-yl)propan-1-one hydrochloride m.p. 123°–126° C., (Found: C, 54.33; H, 4.06; N, 10.36; C₁₈H₁₆Cl₃N₃O requires C, 54.49; H, 3.81; N, 10.59) having the formula:

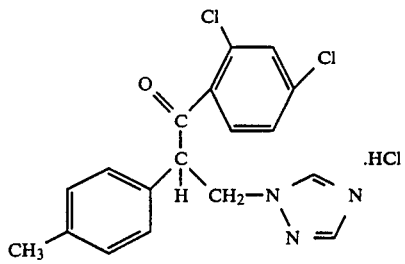

EXAMPLE 17

1-(Imidazol-1-yl)-2-(4-methylphenyl)decan-3-one hydrochloride (Found C, 67.76; H, 8.34; N, 7.82; C₂₀H₂₉ClN₂O.¼H₂O requires C, 67.96; H, 8.13; N, 7.93) having the formula:

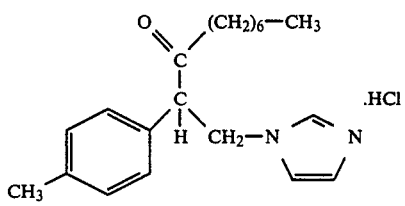

EXAMPLE 18

1-(3,5-Dichlorophenyl)-3-(imidazol-1yl)-2-phenyl propan-1-one m.p. 149°–152° C., (Found C, 62.14; H, 4.03; N, 8.00; C₁₈H₁₄Cl₂N₂O.¼H₂O requires C, 61.97; H, 4.16; N, 8.03) having the formula:

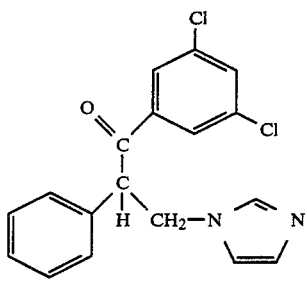

EXAMPLE 19

3-(Imidazol-1-yl)-2-phenyl-1-(3-pyridyl)propan-1-one m.p. 116°–119° C., (Found C, 72.61; H, 5.15; N, 14.98; $C_{17}H_{15}N_3O.2H_2O$ requires C, 72.70; H, 5.48; N, 14.97) having the formula:

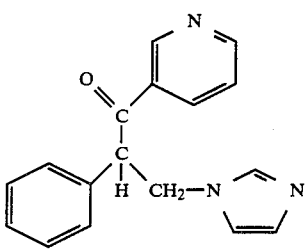

EXAMPLE 20

2-Phenyl-1-(3-pyridyl)-3-(1,2,4-triazol-1-yl)propan-1-one m.p. 76°–79° C., (Found C, 68.35; H, 4.89; N, 20.08; $C_{16}H_{14}N_4O.\frac{1}{8}H_2O$ requires C, 68.51; H, 5.08; N, 19.98) having the formula:

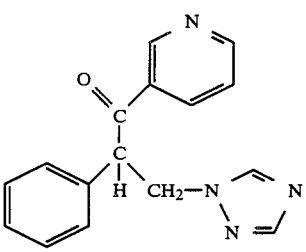

EXAMPLE 21

3-(Imidazol-1-yl)-2-phenyl-1-(2-pyridyl)propan-1-one m.p. 144°–146° C., (Found C, 72.82; H, 5.39; N, 14.97; $C_{17}H_{15}N_3O.\frac{1}{4}H_2O$ requires C, 72.53; H, 5.51; N, 14.91) having the formula:

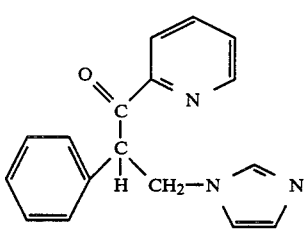

EXAMPLE 22

1-(2,4-Dichlorophenyl)-3,3-dimethyl-2-(imidazol-1-ylmethyl)butan-1-one m.p. 77°–82° C., (Found C, 58.54; H, 5.63; N, 8.44; $C_{16}H_{18}Cl_2N_2O.\frac{1}{4}H_2O$ requires C, 58.44; H, 5.63; N, 8.52) having the formula:

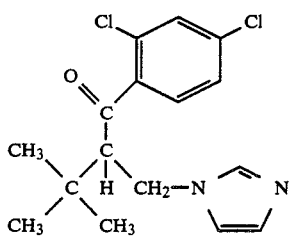

EXAMPLE 23

1-(2,4-Dichlorophenyl)-2-phenyl-3-(1,2,4-triazol-1-yl) propan-1-one m.p. 89°–90° C., (Found C, 58.92; H, 3.83; N, 12.15; $C_{17}H_{13}Cl_2N_3O$ requires C, 58.97; H, 3.78; N, 12.14) having the formula:

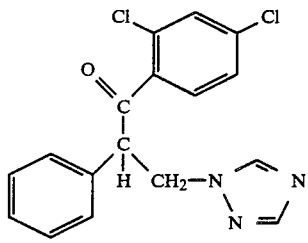

EXAMPLE 24

1-(2,4-Dichlorophenyl)-2-phenyl-3-(2-thiomethylimidazol-1-yl)propan-1-one m.p. 128°–129° C., (Found C, 52.95; H, 3.6; N, 6.4; $C_{19}H_{16}Cl_2N_2OS$ requires C, 53.3; H, 4.0; N, 6.5) having the formula:

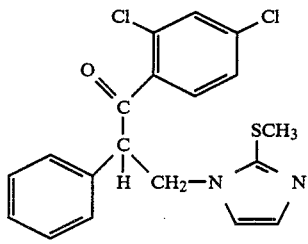

EXAMPLE 25

1,3-Diphenyl-4-(imidazol-1-yl)butan-2-one m.p. 81°–81° C., (Found C, 78.25; H, 5.88; N, 9.53; $C_{19}H_{18}N_2O$ requires C, 78.62; H, 6.21; N, 9.66) having the formula:

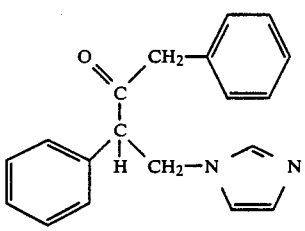

EXAMPLE 26

E-3-[1-[3-(2,4-Dichlorophenyl)-3-oxo-2-phenylpropyl] imidazol-4-yl]propenoic acid A solution of E-3-(imidazol-4(5)-yl)propenoic acid (8 g) in hot dimethylformamide (100 ml) was cooled until crystallization occurred. To the mixture was rapidly added a solution of 1-(2,4-dichlorophenyl)-2-phenylpropen-1-one (4 g) in ethanol (8 ml). The resulting mixture was cooled to 20° C. Ethyl acetate was added and the resulting mixture was washed with water, dried over anhydrous magnesium sulphate and concentrated under reduced pressure to yield a white solid which was repeatedly washed with hexane. Recrystallization of the white solid from ethyl acetate:hexane yielded white crystals of E-3-[1-[3-(2,4-dichlorophenyl)-3-oxo-2-phenylpropyl]imidazol-4-yl] propenoic acid m.p. 229°–231° C. (Found: C, 59.86; H, 3.81; N, 6.60; $C_{21}H_{16}N_2Cl_2O_3 \cdot \frac{1}{2}H_2O$ requires C, 59.45; H, 4.03; N, 6.60) having the formula:

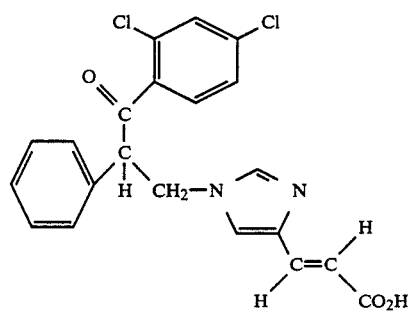

The anti-anaerobic activity of the compounds of the present invention is illustrated by the following Examples.

EXAMPLE 27

The screening panel utilized in this Example consisted of 5 strains of *Bacteroides fragilis*. All assays were carried out in 96 well microtitre plates. If an isolate was obtained from either a culture collection or clinical source, the isolate was immediately inoculated into Wilkins-Chalgren broth (Oxoid) and incubated at 37° C. in an anaerobic chamber in an atmosphere of 85% nitrogen, 10% carbon dioxide, and 5% hydrogen for 48 hours. At the end of this time, the viable count was about $10^{12}$ organisms/ml broth. A 1 ml aliquot of each culture was placed in an ampoule and quick frozen in acetone-dry ice mixture and stored in liquid nitrogen. When an inoculum was utilized in an assay, one of the ampoules was thawed and diluted with fresh broth to yield a suspension having a count of $5 \times 10^5$ organisms/ml. A 100 ul aliquot of the suspension was inoculated into each well of the microtitre plate.

A 2 mg sample of the test compound was dissolved in 0.2 ml of a suitable solvent such as dimethylsulphoxide, polyethylene glycol 200 or methanol. The solution was then diluted with 4.8 ml of water to yield a solution having a concentration of 400 mg/L. Doubling dilutions of this stock were prepared to give a range of concentrations from 1.6–200 mg/L. 100 ul of each concentration are then placed in the wells of the microtitre plate containing the inoculum, to produce a final concentration range of 0.8–100 mg/l. Metronidazole, was employed as a positive control and a solvent/water mixture was employed as a negative control. After addition of the test solution the final inoculum level is $10^5$ cells/ml. The plates were incubated for 48 hours at 37° C. in the anaerobic chamber. The Minimum Inhibitory Concentration (MIC) was read visually. The MIC is defined as the lowest concentration at which there is no detectable growth. The Minimum Bactericidal Concentration (MBC) was determined by taking a 50 ul aliquot from each well and placing it in fresh medium. The MBC is defined as the lowest concentration at which there is less than 5 colonies (i.e., 99.9% reduction in viable count) after 48 hours of incubation. The MIC and MBC values for each compound tested and the respective MIC and MBC value for metronidazole are indicated in Table I. The MIC and MBC value for the negative control that was assayed along with each test compound was greater than 100 mg/L. The MIC and MBC values in Table I are expressed in mg/L. A blank in the table represented by a "—" indicates that the assay was not conducted using the strain indicated.

The strains of *Bacteroides fragilis* utilized in the above procedure are identified by letter in accordance with the following legend:

| STRAIN | ORGANISM |
|---|---|
| A | *B. fragilis* NCTC 10581 |
| B | *B. fragilis* NCTC 9343 |
| C | *B. fragilis* NCTC 9344 |
| D | *B. fragilis* MZ-R ATCC 11295 |
| E | *B. fragilis* WS-1* |

*Obtained from St. Thomas Hospital Medical School, London, United Kingdom

TABLE I

| COMPOUND OF EXAMPLE NO. | STRAIN A MIC | A MBC | B MIC | B MBC | C MIC | C MBC | D MIC | D MBC | E MIC | E MBC |
|---|---|---|---|---|---|---|---|---|---|---|
| 2 | 0.8 | 0.8 | 0.8 | 0.8 | 0.8 | 0.8 | 0.8 | 0.8 | 0.8 | 0.8 |
| Metronidazole | 0.8 | 0.8 | 0.8 | 0.8 | 0.8 | 3.1 | 12.5 | 12.5 | 0.8 | 0.8 |
| 15 | 0.8 | 0.8 | 0.8 | 0.8 | 0.8 | 0.8 | 0.8 | 0.8 | 0.8 | 0.8 |
| Metronidazole | 0.8 | 0.8 | 0.8 | 0.8 | 0.8 | 3.1 | 12.5 | 12.5 | 0.8 | 0.8 |
| 16 | 3.1 | 3.1 | 3.1 | 3.1 | 3.1 | 3.1 | 0.8 | 15. | 1.5 | 3.1 |
| Metronidazole | 0.6 | 1.2 | 0.6 | 1.2 | 0.6 | 1.2 | 10.9 | 10.0 | 1.2 | 1.2 |
| 17 | 12.5 | 100 | 12.5 | 100 | — | — | 3.1 | 100 | 12.5 | 100 |
| Metronidazole | 0.6 | 1.2 | 0.6 | 1.2 | — | — | 10.0 | 10.1 | 1.2 | 1.2 |
| 18 | 0.8 | 1.5 | 1.5 | 1.5 | 0.8 | 0.8 | 0.8 | 1.5 | 1.5 | 12.5 |

TABLE I-continued

| COMPOUND OF EXAMPLE NO. | STRAIN | | | | | | | | | |
|---|---|---|---|---|---|---|---|---|---|---|
| | A | | B | | C | | D | | E | |
| | MIC | MBC | MIC | MBC | MIC | MBC | MIC | MBC | MIC | MBC |
| Metronidazole | 0.6 | 0.6 | 0.6 | 1.2 | 0.3 | 1.2 | 10 | 10 | 0.6 | 1.2 |
| 19 | 12.5 | 50 | 12.5 | 50 | 12.5 | 50 | 12.5 | 50 | 6.2 | 25 |
| Metronidazole | 0.5 | 1.2 | 0.6 | 0.6 | 0.6 | 1.2 | 10 | 10 | 0.6 | 0.6 |
| 20 | 100 | — | 100 | — | 100 | — | 100 | — | 100 | — |
| Metronidazole | 0.6 | 1.2 | 0.6 | 0.6 | 0.6 | 1.2 | 10 | 10 | 0.6 | 0.6 |
| 21 | 12.5 | 12.5 | 25 | 25 | 6.2 | 12.5 | 6.2 | 6.2 | 25 | 25 |
| Metronidazole | 0.6 | 0.6 | 1.2 | 1.2 | 1.2 | 1.2 | 10 | 10 | 1.2 | 1.2 |
| 22 | 50 | — | 50 | — | 50 | — | 50 | — | 100 | — |
| Metronidazole | 0.6 | — | 0.6 | — | 0.3 | — | 10 | 0 | 0.6 | — |
| 23 | 0.8 | 0.8 | 0.8 | 0.8 | 0.8 | 0.8 | 0.8 | 0.8 | 0.8 | 0.8 |
| Metronidazole | 0.8 | 0.8 | 0.8 | 0.8 | 0.8 | 0.8 | 12.5 | 12.5 | 1.5 | 1.5 |
| 24 | 25 | 100 | 25 | 100 | 25 | 100 | 25 | 100 | 50 | 100 |
| Metronidazole | 1.2 | 1.2 | 0.6 | 0.6 | 0.6 | 1.2 | 10 | 10 | 1.2 | 1.2 |
| 25 | 25 | — | 25 | — | 25 | — | 12.5 | — | 25 | — |
| Metronidazole | 0.6 | — | 0.6 | — | 0.3 | — | 10 | — | 0.6 | — |

EXAMPLE 29

Conducting the procedures described in Example 28, the anti-anaerobic activity of certain compounds of the present invention was demonstrated utilizing an additional 12 strains.

The stains of *Bacteroides fragilis* utilized in the Example are identified by letter in accordance with the following legend:

| Strain | Organism |
|---|---|
| F | *Clostridium perfringens* NCTC 523 |
| G | *Clostridium perfringens* NCTC 8237 |
| H | *Clostridium difficile* CI |
| I | *Campylobacter fetus* ATCC 29428 |
| J | *Fusobacterium necrophorum* ATCC 11295 |
| K | *Peptococcus magnus* ATCC 29328 |
| L | *Peptococcus prevotti* ATCC 9321 |
| M | *Peptostreptococcus anaerobicus* ATCC 27337 |
| N | *Propionibacterium acnes* NCTC 737 |
| O | *Propionibacterium acnes* NCTC 7337 |

The MIC values obtained are indicated in Table II. A blank in the table represented by a "—" indicates that the assay was not conducted using the strain indicated.

TABLE II

| Compound of Example No. | MIC STRAIN | | | | | | | | | |
|---|---|---|---|---|---|---|---|---|---|---|
| | F | G | H | I | J | K | L | M | N | O |
| 2 | 0.8 | 0.8 | 0.8 | 0.8 | 0.8 | 0.8 | 0.8 | 0.8 | 0.8 | 0.8 |
| Metronidazole | 0.08 | 2.5 | 0.08 | 10 | 10 | 0.6 | 1.2 | 0.3 | 10 | 10 |
| 15 | 0.3 | 0.6 | — | — | 0.3 | — | — | — | 0.6 | 0.1 |
| Metronidazole | 0.08 | 2.5 | — | — | 10 | — | — | — | 10 | 10 |
| 18 | 3.1 | 3.1 | 1.5 | 3.1 | 6.2 | 3.1 | 3.1 | 6.2 | 6.2 | 3.1 |
| Metronidazole | 0.08 | 1.2 | 0.08 | 10 | 10 | 0.6 | 1.2 | 0.3 | 10 | 10 |
| 25 | 0.8 | 0.8 | 25 | 25 | 100 | 6.2 | 0.8 | 1.5 | 50 | — |
| Metronidazole | 0.08 | 10 | 1.2 | 10 | 10 | 0.6 | 2.5 | 0.3 | 10 | — |

TABLE II-continued

| Compound of Example No. | MIC STRAIN | | | | | | | | | |
|---|---|---|---|---|---|---|---|---|---|---|
| | F | G | H | I | J | K | L | M | N | O |
| ronidazole | | | | | | | | | | |

Although this invention has been described with respect to specific modification, the details thereof are not to be construed as limitations, for it will be apparent that various equivalents, changes and modification may be restored and modification may be resorted to without departing from the spirit and scope thereof and it is understood that such equivalent embodiments are intended to be included therein.

What is claimed is:

1. A compound of the formula:

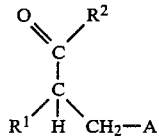

wherein
$R^1$ is phenyl or $C_1$–$C_4$ alkylphenyl;
$R^2$ is dihalophenyl; and
A is imidazol-1-yl 1,2,4-triazol-1-yl or substituted imidazol-1-yl wherein the substituent is one or more groups selected from class consisting of $C_1$–$C_4$ alkylthio and carboxy($C_2$–$C_4$ alkenyl);
and pharmaceutically acceptable acid addition salts thereof.

2. A compound according to claim 1 of the formula

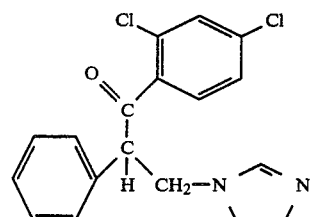

* * * * *